United States Patent [19]

Bennett

[11] Patent Number: 4,925,582
[45] Date of Patent: May 15, 1990

[54] METHODS AND COMPOSITIONS FOR POTENTIATING THE ACTIVITY OF ANTIMICROBAL AGENTS IN INDUSTRIAL WATER BASED FLUIDS

[75] Inventor: Edward O. Bennett, Houston, Tex.
[73] Assignee: OXID, Incorporated, Houston, Tex.
[21] Appl. No.: 202,891
[22] Filed: Jun. 6, 1988
[51] Int. Cl.⁵ .......................................... C10M 173/02
[52] U.S. Cl. .................................. 252/49.3; 252/49.5; 252/51.5 R; 252/77; 72/42
[58] Field of Search .................. 252/49.3, 49.5, 51.5 R
[56] References Cited

U.S. PATENT DOCUMENTS

| | | | |
|---|---|---|---|
| 3,951,833 | 4/1976 | Juda et al. | 252/51.5 R |
| 4,725,613 | 2/1988 | Mahn et al. | 514/375 |
| 4,749,503 | 6/1988 | Bennett et al. | 252/49.3 |

OTHER PUBLICATIONS

Bennett, *Lubrication Engineering* 35:137 (1979).

Schey, *Tribology in Metalworking Fiction, Lubrication and Wear*, pp. 158–159 (1983).

Primary Examiner—William R. Dixon, Jr.
Assistant Examiner—E. McAvoy
Attorney, Agent, or Firm—Arnold, White & Durkee

[57] ABSTRACT

Alkane alkanolamines of the formula $$RNHR^1 OH$$

wherein

R is hydrogen or normal $C_{1-6}$ alkyl; and $R^1$ is a normal or branched chain $C_{2-4}$ alkyl or hydroxymethyl $C_{2-4}$ alkyl are effective to potentiate the activity of and prolong the useful life of antimicrobial agents in controlling the growth of microorganisms in industrial water based fluids. A specific example of the alkanolamines of this invention is n-hexyl ethanolamine.

9 Claims, No Drawings

METHODS AND COMPOSITIONS FOR POTENTIATING THE ACTIVITY OF ANTIMICROBAL AGENTS IN INDUSTRIAL WATER BASED FLUIDS

BACKGROUND OF THE INVENTION

Antimicrobial compositions are generally added to various kinds of industrial water based fluids to reduce or inhibit the growth of microorganisms. In particular, a wide variety of industrial water based fluids such as metal-working fluids, latex paints, water based hydraulic fluids, require antimicrobial compositions to control the growth microorganisms which eventually render the fluids rancid.

One of the problems often associated with water based fluids is the susceptibility of the fluid to the infestation and growth of various microorganisms such as bacteria and fungi (which particularly feed on the organic components thereof). The presence and buildup of such microorganisms can often lead to interference of mechanical operations as a result of the clogging of filters, buildup of slime and sludge, development of odors, rust, emulsion instability, reduced tool life and poor finish. Furthermore, where the workers' hands necessarily come in contact with these deteriorated fluids, usually containing finely divided sharp metal cuttings, serious problems of dermatitis may arise. These and other such similar problems have resulted in the continuing need for better antimicrobial additives for industrial water based fluids. Much effort has been devoted in recent years to controlling this problem; however, it continues to be a major annoyance which costs industry many millions of dollars each year.

Antimicrobial agents constitute an important ingredient of industrial fluids which are commonly depleted faster than the other components of the fluids. Quite often, additional antimicrobial agents must be added to the industrial water based fluid at periodic intervals in order to compensate for their loss from the fluid after continuous use.

Preservatives are removed from the fluid after interacting with the microbes to bring about their inhibition or death. The greater the microbial population, the more quickly they are lost from the system. Thus, the concentration of any preservative declines with time and may be reduced to subinhibitory levels in only a few days.

A number of suggestions have been made for inhibiting the growth of bacteria in aqueous fluids such as those described in U.S. Pat. Nos. 4,172,140, 3,951,830, 3,799,876, 3,515,671, and 2,976,244. The use of various formaldehyde preservatives for metalworking fluids including monomethylol dimethyl hydantoin and dimethylol dimethyl hydantoin has also been proposed (see Bennett, E. O., *Int. Biodetn. Bull.* 9: 95–100 (1973) and Maeda et al, *Agr. Biol. Chem.*, 40: 1111–2222 (1976)).

Gray and Wilkinson in *J. Gen. Microbiol.*, 39: 385–399 (1965) and *J. App. Bact.*, 28: 153–164 (1965) describe the action of the ethylenediaminetetraacetic acid (EDTA) on some bacteria. The effectiveness of such chelating agents as EDTA along for bacterial control in aqueous systems is disputed as evidenced by U.S. Pat. Nos. 3,240,701, 3,408,843, and 3,591,679.

The antimicrobial compositions used in industrial water based fluids seem to suffer from one or more disadvantages including high cost, unacceptable toxicity or low degree of effectiveness at the present state of the art.

The present invention provides agents which when combined with antimicrobial agents are effective to potentiate the activity of the antimicrobial agent in controlling the growth of microorganisms in industrial water based fluids. Hence, less antimicrobial agent is required to produce the same antimicrobial effect as compared to using the antimicrobial agent alone.

SUMMARY OF THE INVENTION

The present invention provides antimicrobial potentiating agents. The antimicrobial potentiating agents of the invention are alkanolamines and alkyl alkanolamines of the formula:

$$RNHR^1OH$$

wherein

R is hydrogen or normal $C_{1-6}$ alkyl; and $R^1$ is a normal or branched chain $C_{2-4}$ alkyl or hydoxymethyl $C_{2-4}$ alkyl.

Representative examples of alkanolamines which potentiate the activity of antimicrobial agents include n-hexyl ethanolamine, 2-methyl ethanolamine, 2-hydroxymethyl ethanolamine, n-amyl ethanolamine, 2-amine-1-butanol, 3-amino-1-propanol, and isopropanolamine.

The alkanolamines of this invention when combined with antimicrobial agents are effective to potentiate the activity of and extend the useful life the antimicrobial agents in preventing and controlling the fouling of industrial water based fluids. In particular, the use of the antimicrobial potentiating agents of the invention reduces the amount of antimicrobial agent needed to effect a desired control of microbial (including bacterial and fungal) growth in industrial water based fluids. Alternatively, the use of the antimicrobial potentiating agents of this invention can extend the useful life of the antimicrobial agent used to control microbial growth in industrial water based fluids. For example, 500–1500 ppm of the antimicrobial potentiating agents can reduce the needed amount of anitmicrobial agent by about 20–50%. Alternatively, 500–1500 ppm of the antimicrobial potentiating agent admixed with an antimicrobial agent will extend the normal useful life of the antimicrobial agent by about 20–100% or more.

In the context of this invention, the amount of potentiating agent added to the industrial water fluid does not by itself exhibit sufficient activity to control microbial growth in the fluid.

DETAILED DESCRIPTION OF THE INVENTION

The present invention provides compositions of antimicrobial potentiating agents together with antimicrobial agents. The compositions of the present invention when added to industrial water based fluids are useful to control the growth of microorganisms, including for example bacteria, algae and fungi, which tend to foul the industrial waters.

In the context of this invention, the term "industrial water based fluid" is meant to encompass water, oil in water, water in oil emulsions and like compositions which are susceptible to the infestation and growth of microorganisms. Thus, for example, soaps and detergent fluids, cosmetics, latex paints, paper pulping fluids, drilling muds, water based hydraulic fluids, water for coolant towers, metalworking fluids or cutting fluids, are included.

As used herein, the term "antimicrobial effective amount" means that amount of the antimicrobial agent which when added to the industrial water based fluid will adequately inhibit the growth of microorganisms in that fluid. The term "antimicrobial potentiating effective amount" or words to that effect, mean the amount of the antimicrobial potentiating agent which when combined with the antimicrobial agent is effective to enhance the activity of or prolong the useful life of the antimicrobial agent in controlling the growth of microorganisms in the industrial water based fluids.

Generally, from about 500 to 1500 parts of the alkanolamine, antimicrobial potentiating agent are admixed with the recommended effective amount of the antimicrobial agent per million parts of the industrial water based fluid.

In general, the antimicrobial agents which are potentiated by the alkanolamines of this invention include triazines, phenols, morpholines, "formaldehyde releasers (compounds which will hydrolyze into formaldehyde and other non-persistent fragments in aqueous solution including, e.g., tris(hydroxymethyl)nitromethane, hexahydro-1,3,5-tris(2-hydroxyethyl)-S-triazine, hexahydro-1,3,5-triethyl-S-triazine, hexahydro-1,3,5-tris(2-hydroxyethyl)-S-triazine iodine complex, and 1-(3-chloroallyl)-3,5,7-triaza-1-azoniaadamantane chloride)," azoniatricylodecanes, omadines and oxazolidines. Commericial products of such agents are currently marketed under the tradenames: Triadine 10, Grotan, Vancide TH, Dowicil, Dowicide A, Bioban P-1487, Tris Nitro, Busan 1024, Cosan 101, Nuosept 95.

The following examples are offered to more fully illustrate the invention, but are not intended to limit the scope thereof.

Experimental Procedures

The test units consisted of quart jars placed in rows. Above each row, a metal framework was constructed to support the aeration system which consisted of aquarium valves connected together with plastic tubing. The amount of aeration of each unit was controlled by adjusting the valves. Capillary pipettes were employed as aerators to produce a fine steam of bubbles in the diluted coolants.

Five hundred ml of tap water (120 ppm hardness) was added to each jar. The n-hexyl ethanolamine and selected antimicrobial agent were added to each jar along with 15.0 ml of cutting fluid concentrate to produce the desired coolant concentration. Each unit was then made up to a total volume of 600.0 ml by adding additional tap water.

Each test unit was inoculated with a mixture of bacteria and fungi which were obtained and maintained as described in Bennett, "The Deterioration of Metal Cutting Fluids", *Prog. Indust. Microbiol.* 13: 121–249 (1974), the entire contents of which are incorporated herein by reference. Each unit was inoculated once each week with 1.0 ml of a 50–50 mixture of both inocula.

Each unit was examined once each week for its microbial content for as long as the count remained below 100,000 organisms/ml. Two consecutive counts in excess of this figure at weekly intervals was considered to constitute a failure and the test was discontinued at that time.

Two different types of control experiments were included. Each shipment of fresh coolant was tested upon arrival to determine if the product exhibited any inhibitory properties, as defined in the previous paragraph. All of the coolants used in the investigation were especially prepared by coolant manufacturers for this work and they did not contain a preservative. None of the products employed in this investation exhibited any inhibitory properties and failed in the first week of testing. The second set of controls consisted of a particular cutting fluid preserved with a commonly used antimicrobial agent. Normally, these control units failed within 21 days due to mold growth. The controls functioned normally during the test period. A third control consisted of representative cutting fluids with added n-hexyl ethanolamine. Normally, such controls failed within less than 7 days.

Since the test units were under constant aeration, there was considerable evaporation from each unit. The units were calibrated at the 600.0 ml mark and, once or twice each week, depending upon environmental conditions, distilled water was added to each unit to bring the liquid level back to this mark. Distilled water was used in order to avoid a buildup of inorganic salts in the test units.

Results

A series of sample jars were prepared according to the procedure outlined above to ascertain the antimicrobial potentiating effects of n-hexyl ethanolamine (HEA) when admixed with a selected antimicrobial agent. The sample coolants were mixed with water in a ratio of 1:40 (coolant to water). The results are set forth below, wherein the time in days is recorded when the microbial count in such test reached the level of 100,000 or the test discontinued.

The n-hexyl ethanolamine used in these examples was prepared according to the alternate synthesis scheme described in U.S. Pat. No. 4,749,503, issued Jun. 7, 1988.

As used in the following tables, the underlined numbers indicate that the test failed due to slime at the time noted, and the * means the test continued to show inhibitory action at the time the test was discontinued.

TABLE 1

EFFECTIVENESS OF DIFFERENT COMBINATIONS OF HEA AND GROTAN IN CUTTING FLUIDS

| Compound | Concentration in ppm | | | | | | |
|---|---|---|---|---|---|---|---|
| Grotan | 500 | 1000 | 1500 | | | | |
| HEA | | | | 500 | 1000 | 1500 | |
| Coolant | Days of control | | | | | | |
| IRMCO emulsion | 7 | 21 | 14 | 0 | 7 | 7 | |
| Monroe Primecut | 7 | 21 | 21 | 0 | 0 | 0 | |
| Stuart emulsion | 7 | 21 | 14 | 0 | 0 | 0 | |
| Sanson coolant | 7 | 21 | 14 | 0 | 7 | 14 | |
| Buckeye emulsion | 7 | 21 | 14 | 0 | 7 | 7 | |
| Compound | Concentration in ppm | | | | | | |
| Grotan | 500 | 500 | 1000 | 1000 | 1500 | 1500 | 1500 |
| HEA | 1000 | 1500 | 500 | 1000 | 500 | 1000 | 1500 |
| Coolant | Days of control | | | | | | |
| IRMCO emulsion | 28 | 49 | 21 | 35 | 42 | 35 | 70 |
| Monroe Primecut | 48 | 42 | 28 | 35 | 21 | 35 | 84 |
| Stuart emulsion | 14 | 42 | 21 | 21 | 28 | 21 | 91 |
| Sanson coolant | 21 | 84 | 21 | 28 | 28 | 35 | 98 |
| Buckeye emulsion | 63 | 91 | 84 | 98 | 77 | 91 | 105* |

TABLE 2

EFFECTIVENESS OF DIFFERENT COMBINATIONS OF HEA AND BIOBAN P-1487 IN CUTTING FLUIDS

| Compound | Concentration in ppm | | | | | | |
|---|---|---|---|---|---|---|---|
| Bioban P-1487 | 250 | 500 | 1000 | 500 | 250 | 500 | 1000 |
| HEA | | | | 500 | 1500 | 1500 | 1500 |
| Coolants | Days of stability | | | | | | |
| IRMCO emulsion | 0 | 14 | 35 | 21 | 28 | 42 | 84 |
| Monroe Primecut | 28 | 56 | 84 | 14 | 35 | 56 | 63 |
| Stuart emulsion | 7 | 42 | 49 | 21 | 21 | 42 | 56 |
| Sanson coolant | 7 | 35 | 42 | 21 | 21 | 112 | 140* |
| Buckeye emulsion | 35 | 42 | 49 | 35 | 119 | 112 | 140* |

TABLE 3

EFFECTIVENESS OF DIFFERENT COMBINATIONS OF HEA AND NA OMADINE IN CUTTING FLUIDS

| Compound | Concentration in ppm | | | | | | | | |
|---|---|---|---|---|---|---|---|---|---|
| Na Omadine | 100 | 250 | 500 | 100 | 100 | 250 | 250 | 500 | 500 |
| HEA | | | | 1500 | 2000 | 1500 | 2000 | 1000 | 1500 |
| Coolants | Days of stability | | | | | | | | |
| IRMCO | 0 | 0 | 0 | 14 | 105 | 28 | 119 | 7 | 112 |
| Monroe | 0 | 0 | 21 | 28 | 196* | 28 | 119 | 7 | 28 |
| Stuart | 0 | 21 | 35 | 42 | 147 | 49 | 119 | 49 | 112 |
| Sanson | 0 | 7 | 21 | 21 | 77 | 28 | 112 | 7 | 140* |
| Buckeye | 0 | 21 | 21 | 42 | 196* | 140* | 140* | 77 | 140* |

TABLE 4

EFFECTIVENESS OF DIFFERENT COMBINATIONS OF HEA AND TRIADINE 10 IN CUTTING FLUIDS

| Compound | Concentration in ppm | | | | | | | |
|---|---|---|---|---|---|---|---|---|
| Triadine 10 | 250 | 500 | 1000 | 250 | 250 | 500 | 500 | 1000 |
| HEA | | | | 1500 | 2000 | 1000 | 1500 | 1500 |
| Coolant | Days of stability | | | | | | | |
| IRMCO emulsion | 21 | 28 | 35 | 28 | 77 | 63 | 56 | 175 |
| Monroe Primecut | 49 | 49 | 77 | 42 | 84 | 49 | 42 | 112 |
| Stuart emulsion | 35 | 77 | 98 | 42 | 91 | 70 | 98 | 161 |
| Sanson coolant | 28 | 42 | 56 | 77 | 63 | 42 | 140* | 182* |
| Buckeye coolant | 35 | 49 | 42 | 140* | 105* | 105* | 140* | 182* |

*Still inhibitory when taken off test

TABLE 5

EFFECTIVENESS OF DIFFERENT COMBINATIONS OF HEA AND AMINE CS 1135 IN CUTTING FLUIDS

| Compound | Concentration in ppm | | | | | | |
|---|---|---|---|---|---|---|---|
| Amine CS 1135 | 500 | 1000 | | | 1000 | 500 | 1000 |
| HEA | | | 1000 | 1500 | 1000 | 1500 | 1500 |
| Coolants | Days of stability | | | | | | |
| IRMCO emulsion | 28 | 28 | 7 | 7 | 49 | 35 | 84 |
| Monroe Primecut | 28 | 28 | 0 | 0 | 35 | 35 | 77 |
| Stuart emulsion | 28 | 21 | 0 | 0 | 49 | 35 | 84 |
| Sanson coolant | 28 | 14 | 7 | 14 | 35 | 35 | 91 |
| Buckeye emulsion | 28 | 14 | 7 | 7 | 84 | 48 | 126 |

TABLE 6

EFFECTIVENESS OF HEA AND COSAN 101 IN CUTTING FLUIDS

| Coolants | 1000 ppm Cosan 101 | 1500 ppm HEA | Combination of both |
|---|---|---|---|
| IRMCO emulsion | 14 | 7 | 84 |
| Monroe emulsion | 21 | 0 | 91 |
| Stuart emulsion | 21 | 0 | 70 |
| Sanson coolant | 21 | 14 | 98 |
| Buckeye emulsion | 21 | 7 | 140* |

TABLE 7

EFFECTIVENESS OF HEA IN COMBINATION WITH BUSAN 85 IN CUTTING FLUIDS

| Coolants | 1000 ppm Busan 85 | 1500 ppm HEA | Combination of both |
|---|---|---|---|
| IRMCO emulsion | 7 | 7 | 63 |
| Monroe Primecut | 7 | 0 | 7 |
| Stuart emulsion | 14 | 0 | 91 |
| Sanson coolant | 7 | 14 | 49 |
| Buckeye emulsion | 7 | 7 | 140* |

TABLE 8

EFFECTIVENESS OF HEA IN COMBINATION WITH BUSAN 1024 IN CUTTING FLUIDS

| Coolants | 1000 ppm Busan 1024 | 1500 ppm HEA | Combination of both |
|---|---|---|---|
| IRMCO emulsion | 0 | 7 | 14 |
| Monroe Primecut | 0 | 0 | 7 |
| Stuart emulsion | 7 | 0 | 7 |
| Sanson coolant | 0 | 14 | 7 |
| Buckeye emulsion | 0 | 7 | 49 |

TABLE 9

EFFECTIVENESS OF HEA IN COMBINATION WITH TRIS NITRO IN CUTTING FLUIDS

| Coolants | 1000 ppm Tris Nitro | 1500 ppm HEA | Combination of both |
|---|---|---|---|
| IRMCO emulsion | 7 | 7 | 0 |
| Monroe Primecut | 49 | 0 | 35 |
| Stuart emulsion | 0 | 0 | 28 |
| Sanson coolant | 14 | 14 | 42 |
| Buckeye emulsion | 7 | 7 | 56 |

TABLE 10

EFFECTIVENESS OF HEA IN COMBINATION WITH AMINE CS-1246 IN CUTTING FLUIDS

| Coolants | 1000 ppm CS-1246 | 1500 ppm HEA | Combination of both |
|---|---|---|---|
| IRMCO emulsion | 7 | 7 | 21 |
| Monroe Primecut | 7 | 0 | 42 |
| Stuart emulsion | 7 | 0 | 21 |
| Sanson coolant | 7 | 14 | 21 |
| Buckeye emulsion | 7 | 7 | 105* |

TABLE 11

EFFECTIVENESS OF HEA IN COMBINATION WITH NUOSEPT 95 IN CUTTING FLUIDS

| Coolants | 1000 ppm Nuosept 95 | 1500 ppm HEA | Combination of both |
|---|---|---|---|
| IRMCO emulsion | 7 | 7 | 28 |
| Monroe Primecut | 7 | 0 | 28 |
| Stuart emulsion | 0 | 0 | 21 |
| Sanson coolant | 7 | 14 | 21 |
| Buckeye emulsion | 7 | 7 | 105* |

TABLE 12

EFFECTIVENESS OF HEA IN COMBINATION WITH TROYSAN 174 IN CUTTING FLUIDS

| Coolants | 1000 ppm Troysan 174 | 1500 ppm HEA | Combination of both |
|---|---|---|---|
| IRMCO emulsion | 28 | 0 | 98 |
| Monroe Primecut | 42 | 14 | 98 |
| Stuart emulsion | 28 | 0 | 84 |
| Sanson coolant | 28 | 14 | 91 |
| Buckeye emulsion | 28 | 21 | 136 |

Grotan is 78.5% active solution of hexahydro-1,3,5-tris (2-hydroxyethyl)-S-triazine.

Bioban P-1487 is a mixture of 70% 4-(2-nitrobutyl) morpholine and 20% 4,4-(2-ethyl-2-nitromethylene) dimorpholine.

Triadine 10 is a mixture of sodium 2-pyridinethiol-1-oxide 6.4% and hexahydro-1,3,5-tris-(2-hydroxyethyl)-S-triazine 63.6%.

Amine CS 1246 is 4,4-dimethyloxazolidine p-toluenesulfonic acid.

Cosan 101 is 74.9% 4,4 dimethyloxazolidine and 2.8% 3, 4, 6 trimethyloxazolidine.

Busan 85 is 90% by weight of barium metaborate.

Busan 1024 is a 40% aqueous solution of sodium salt of 1-carboxymethyl-3,5,7-triaza-1-azoniatricyclodecane chloride.

Tris Nitro is a 50% active solution of tris(hydroxymethyl)-nitromethane.

Nuosept 95 is a mixture of bicylicpolyoxymethylene oxazolidines.

Troysan 174 is 2-hydroxymethyl ethanolamine.

While the invention has been explained in relation to certain illustrative embodiments of it, it is understood that many modifications and substitutions may be made in any of the specific embodiments within the scope of the appended claims which are intended also to cover equivalents of them.

What is claimed is:

1. An antimicrobial composition comprising an antimicrobial potentiating mixture of an antimicrobial agent and one or both of n-hexyl ethanolamine or n-amyl ethanolamine.

2. The antimicrobial composition of claim 1 wherein the antimicrobial potentiating agent is n-hexyl ethanolamine.

3. The antimicrobial composition of claim 1 wherein the antimicrobial agent is a triazine, oxazolidine, formaldehyde releaser, 1,10 phenanthroline, morpholine, phenol, azoniatricyclodecane, omadine or nitromethane.

4. A method for potentiating the effectiveness of an antimicrobial agent in controlling the growth of microorganisms in an industrial water based fluid comprising adding to the fluid an antimicrobially effective amount of an antimicrobially potentiating mixture of the antimicrobial agent and one or both of n-hexyl ethanolamine or n-amyl ethanolamine.

5. The method of claim 4 wherein the antimicrobial potentiating agent is n-hexyl ethanolamine.

6. The method of claim 4 wherein the antimicrobial agent is a triazine, oxazolidine, formaldehyde releaser, 1,10 phenanthroline, morpholine, phenol, azoniatricyclodecane, omadine or nitromethane.

7. The method of claim 4 wherein the amount of n-hexyl ethanolamine or n-amyl ethanolamine added to the fluid ranges from 500 to 1500 ppm of the fluid.

8. The antimicrobial composition of claim 1 wherein the antimicrobial agent and n-hexyl ethanolamine or n-amyl ethanolamine are in ratio of 1:6 to 1:1 by weight.

9. The method of claim 4 wherein the antimicrobial agent and n-hexyl ethanolamine or n-amyl ethanolamine are added in ratio of 1:6 to 1:1 by weight.

* * * * *